(12) United States Patent
Ikemoto

(10) Patent No.: US 6,183,845 B1
(45) Date of Patent: Feb. 6, 2001

(54) MULTIPLE LAYER SOFTGEL

(75) Inventor: Lee Ikemoto, Culver City, CA (US)

(73) Assignee: Banner Pharmacaps, Inc., High Point, NC (US)

( * ) Notice: Under 35 U.S.C. 154(b), the term of this patent shall be extended for 0 days.

(21) Appl. No.: 09/318,709

(22) Filed: May 26, 1999

Related U.S. Application Data

(62) Division of application No. 08/967,969, filed on Nov. 12, 1997, now abandoned.

(51) Int. Cl.[7] .................................................. B32B 7/02
(52) U.S. Cl. .................. 428/213; 428/478.2; 428/476.9; 428/474.7; 428/172; 424/456; 424/472; 424/478
(58) Field of Search .................... 428/478.2, 426.6, 428/474.7, 156, 172, 189, 213; 424/456, 478, 472

(56) References Cited

U.S. PATENT DOCUMENTS

| | | | |
|---|---|---|---|
| 1,924,010 | * 8/1933 | Wickham | 18/15 |
| 2,052,695 | * 9/1936 | Chiverton | 18/15 |
| 2,339,114 | * 1/1944 | Scherer | 18/15 |
| 2,379,831 | * 4/1945 | Scherer | 18/15 |
| 2,387,747 | * 10/1945 | Cowley | 18/21 |
| 2,815,533 | * 12/1957 | Ericson | 18/15 |
| 3,656,997 | * 4/1972 | Cordes | 117/73 |
| 3,959,540 | * 5/1976 | Leiberich et al. | 428/35 |
| 4,350,679 | * 9/1982 | Mizuno et al. | 424/38 |
| 4,817,367 | 4/1989 | Ishikawa et al. | 53/454 |
| 5,256,347 | * 10/1993 | Hayward | 264/171 |
| 5,330,835 | * 7/1994 | Kikuchi et al. | 428/402.22 |
| 5,362,564 | * 11/1994 | Suzuki et al. | 428/402.2 |
| 5,422,160 | * 6/1995 | Ratko et al. | 428/141 |
| 5,672,300 | * 9/1997 | Schurig et al. | 264/4 |
| 5,814,338 | * 9/1998 | Veronesi | 424/472 |

FOREIGN PATENT DOCUMENTS

| | | |
|---|---|---|
| 572942 B1 | 4/1997 | (EP) . |
| 645357 | 11/1950 | (GB) . |
| 96/01612 A1 | * 1/1996 | (WO) . |

* cited by examiner

Primary Examiner—Bruce Hen
Assistant Examiner—B. Shewareged
(74) Attorney, Agent, or Firm—Rhodes & Mason, P.L.L.C.

(57) ABSTRACT

A device, and a method for forming a softgel having multiple gelatin layers and softgels having multiple gelatin layers are disclosed. In particular there is provided a device for forming a gelatin sheet having at least two gelatin layers. Each gelatin layer has a thickness. The device comprises a gelatin spreader box which includes at least one opening for extruding a gelatin sheet. The device also includes a first and a second height adjustable gate disposed at least partially across the opening; and a first and a second height adjustment control. Adjustment of the first height adjustment control varies the height of the first gate and adjustment of the second height adjustment control varies the height of the second gate, thereby controlling the thickness of the at least two gelatin layers.

25 Claims, 6 Drawing Sheets

MULTIPLE LAYER SOFTGEL

This is a division of application Ser. No. 08/967,969 filed on Nov. 12, 1997, abandoned.

FIELD OF THE INVENTION

The present invention relates to a multiple, adjustable gate spreader box and to softgels having multiple gelatin layers.

BACKGROUND OF THE INVENTION

Apparatus for extruding sheets of material are known in the art. For example, Chiverton U.S. Pat. No. 2,052,695 discloses a device for producing films or foils from cellulose acetate. Wickham U.S. Pat. No. 1,924,010 discloses a device for casting double films of materials such as cellulose acetate. Hayward, U.S. Pat. No. 5,256,357 discloses an apparatus for forming non-gelatin, polymeric films of two or more layers. The films are formed by a die having fixed, non-adjustable extrusion slots.

Apparatus for extruding gelatin sheets are also known in the art. Ericson, U.S. Pat. No. 2,815,533 discloses a gelatin encapsulating spreader box which uses a single adjustable doctor blade to vary the thickness of a gelatin layer. Scherer, U.S. Pat. No. 2,339,114 discloses a spreader box for forming a gelatin layer which uses a single adjustable doctor blade to vary the thickness of a gelatin layer.

Capsules of more than one layer are also known. Scherer, U.S. Pat. No. 2,379,831 discloses a gelatin capsule which can include multiple layers. However, the substance forming the additional layer is disclosed as being other than gelatin, because a fill material in the capsule is incompatible with gelatin. Also, the capsules are formed by nozzle extrusion. Kikuchi, U.S. Pat. No. 5,330,835 and Suzuki, U.S. Pat. No. 5,362,564 also disclose a gelatin capsule which can include multiple layers. The substance forming the additional layer is disclosed as being other than gelatin, because a fill material in the capsule is incompatible with gelatin. Also, the capsules are formed by nozzle extrusion. Mizuno, U.S. Pat. No. 4,350,679 discloses a gelatin capsule coated with a wax, such as carnauba wax. The use of wax instead of an additional gelatin layer is taught as preventing problems associated with having an external gelatin layer.

It would be desirable to have softgel capsules which can exhibit different properties such as the degree of permeability, rate of dissolution, mouth feel, taste, and color. These different properties can be provided by producing capsules having more than one layer of gelatin. It also would be desirable to produce a softgel capsule of more than one color, for example, a light color such as yellow and a dark color such as blue, in which the dark color did not rub off on the light color when a number of softgels are in contact with each. Application of a clear gelatin layer over the colored gelatin layer can eliminate such color transfer problems.

Accordingly, it would be desirable to provide a gelatin spreader box that allows for the extrusion of two separate gelatin layers which can vary in thickness and in other properties such as the degree of permeability, rate of dissolution, mouth feel, taste and color, and to provide multiple layer softgels.

SUMMARY OF THE INVENTION

In accordance with one aspect of the present invention, there is provided a device for forming a gelatin sheet having at least two gelatin layers. Each gelatin layer has a thickness. The device comprises a gelatin spreader box having at least one opening for extruding a gelatin sheet. The device includes first and second height adjustable gates disposed at least partially across the opening; and first and second height adjustment controls. Adjustment of the first height adjustment control varies the height of the first gate and adjustment of the second height adjustment control varies the height of the second gate, thereby controlling the thickness of the at least two gelatin layers.

In accordance with another aspect of the present invention, there is provided a softgel capsule which includes a first gelatin layer having a thickness and a second gelatin layer having a thickness. The second gelatin layer at least partially surrounds the first gelatin layer.

In accordance with a further aspect of the present invention, there is provided a system for forming softgel capsules comprising two of the devices as described above and two rotary dies adapted to receive two gelatin sheets.

In accordance with another aspect of the present invention there is provided a method for making a softgel comprising a first gelatin sheet and a second gelatin sheet. The method includes the steps of: extruding first and second gelatin layers from a first device as described above to form a first gelatin sheet; Extruding third and fourth gelatin layers from a second device of claim 1 to form a second gelatin sheet; injecting a fill between the first and second gelatin sheets; and sealing the first and second gelatin sheets together to form the softgel.

Other features and advantages of the invention will become apparent from the following detailed description, taken in conjunction with the accompanying drawings which illustrate, by way of example, various features of preferred embodiments of the invention.

DESCRIPTION OF THE FIGURES

The detailed description of the invention will be made with reference to the accompanying drawings, where like numerals designate corresponding parts of the figures. The drawings are meant to be generally illustrative of various examples of the present invention, but are merely examples and are not meant to be limiting of the scope of the invention.

DETAILED DESCRIPTION OF THE INVENTION

Figure 1:
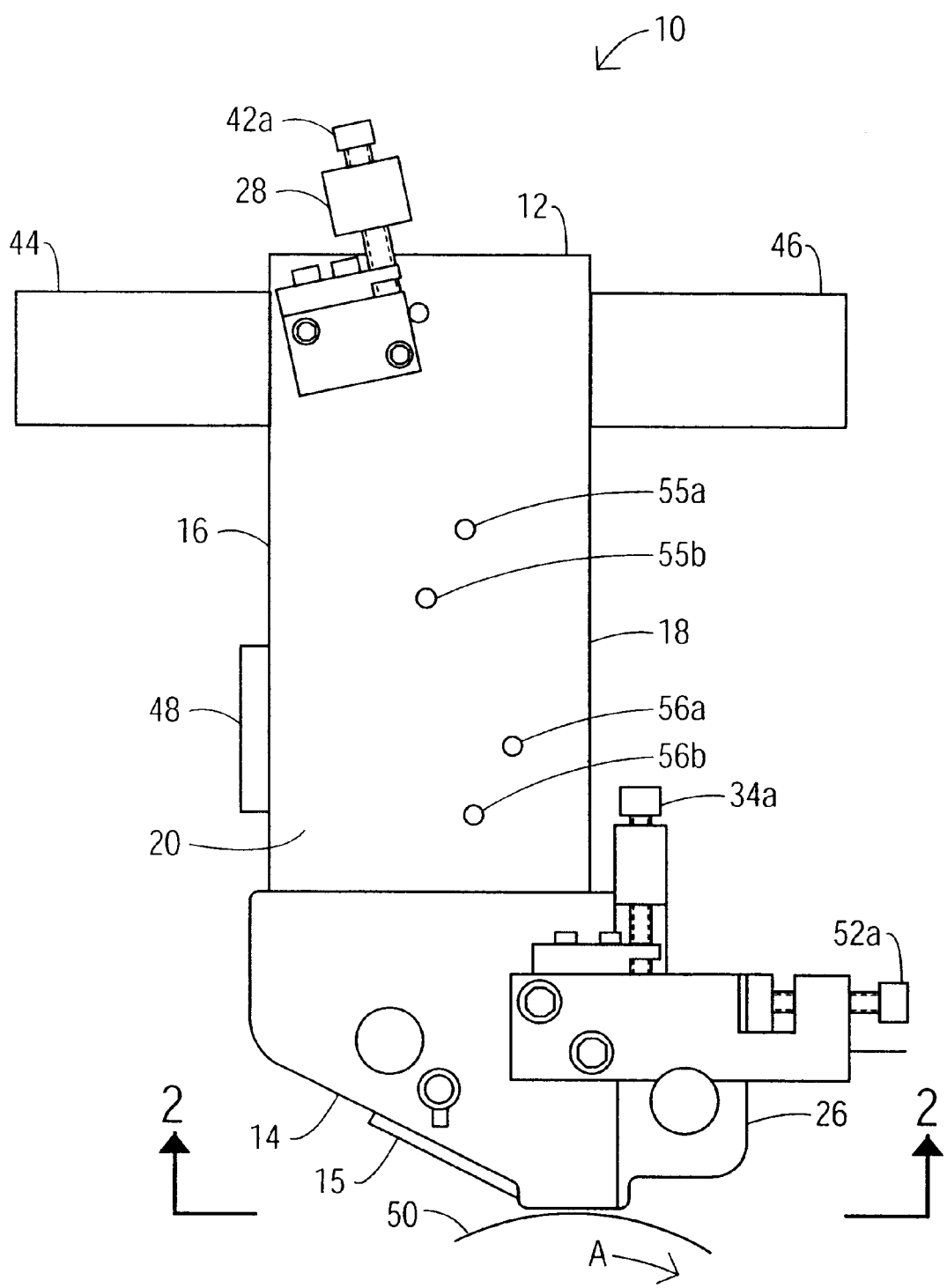
FIG. 1 is a side view of a gelatin spreader box of the present invention.
Figure 7A:
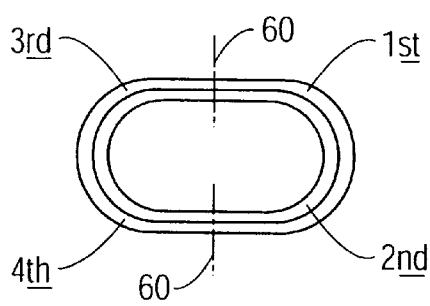
FIG. 7a is a cross section of an exemplar softgel having two opposed sheets, each having two layers stacked upon each other with an environmental seam line shown in broken lines.
Figure 7B:
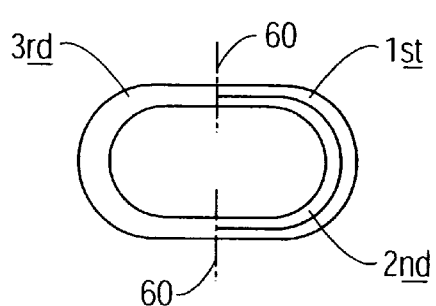
FIG. 7b is a cross section of an exemplar softgel having two opposed sheets, one sheet having two layers stacked upon each other with an environmental seam line shown in broken lines.

As depicted in FIGS. 1–6, spreader box 10 includes a top 12, a bottom 14, a back side 16, a front side 18, and opposed sides 20 and 22. Spreader box 10 is affixed to a standard softgel forming apparatus (not shown) by coupling 48, which can be threaded. Spreader box 10 is preferably formed of a heat conducting and durable material. More preferably spreader box 10 is formed of metal, such as but not limited to brass, aluminum, copper and bronze. Spreader box 10 can be provided in different sizes. For example, spreader box 10 can be about 6 inches wide or about 10.5 inches wide. Most preferably Spreader box 10 is affixed to the softgel forming apparatus so that it is suspended over a rotary die drum 50 as depicted in FIG. 1. Rotary die drum 50 turns in the direction of arrow A. It is to be understood that a second softgel forming apparatus including a second spreader box 10 positioned over a rotary die drum turning in a direction opposite to the direction of rotation depicted by arrow A is used to form softgels of the present invention as described in more detail below. The second spreader box 10 can be a spreader box which forms a multiple layer gelatin sheet as disclosed herein or can be a standard gelatin box which forms a single layer sheet. When a single layer sheet and a multiple layer sheet are formed into a capsule, preferably the thickness of the single layer sheet is adjusted to be about equal to that of the multiple layer sheet as illustrated in FIG. 7b.

Spreader box 10 includes a first gelatin holding chamber 47 formed by front side 18, opposed sides 20 and 22, a first height adjustable gate 26 and a plate 40 of a second height adjustable gate 28. Plate 40 is positioned and retained in chamber 47 by guides 55a and 55b and 56a and 56b disposed adjacent side 20 and corresponding guides disposed adjacent side 22. Molten gelatin is supplied to chamber 47 by gelatin supply pipe 46. Spreader box 10 includes a second gelatin holding chamber 45 formed by back side 16, bottom 14, opposed sides 20 and 22, and plate 40 of second height adjustable gate 28. Molten gelatin is supplied to chamber 45 by gelatin supply pipe 44. Plate 40 has a top, a bottom, a back side, a front side and two opposed sides. Plate 40 preferably extends across spreader box 10 spanning opposed sides 20 and 22 and spanning from top 12 to opening 24. However, in another embodiment plate 40 can extend less than the entire distance between opposed sides 20 and 22, if plate 40 includes flanges 57a and 57b along its side edges, as shown in cross-section in FIG. 5, which will retain molten gelatin therein.

Plate 40 is preferably formed of a heat conducting and durable material, preferably a metal. However, other materials such as but not limited to plastics, composites and combinations thereof can be used.

Figure 2:
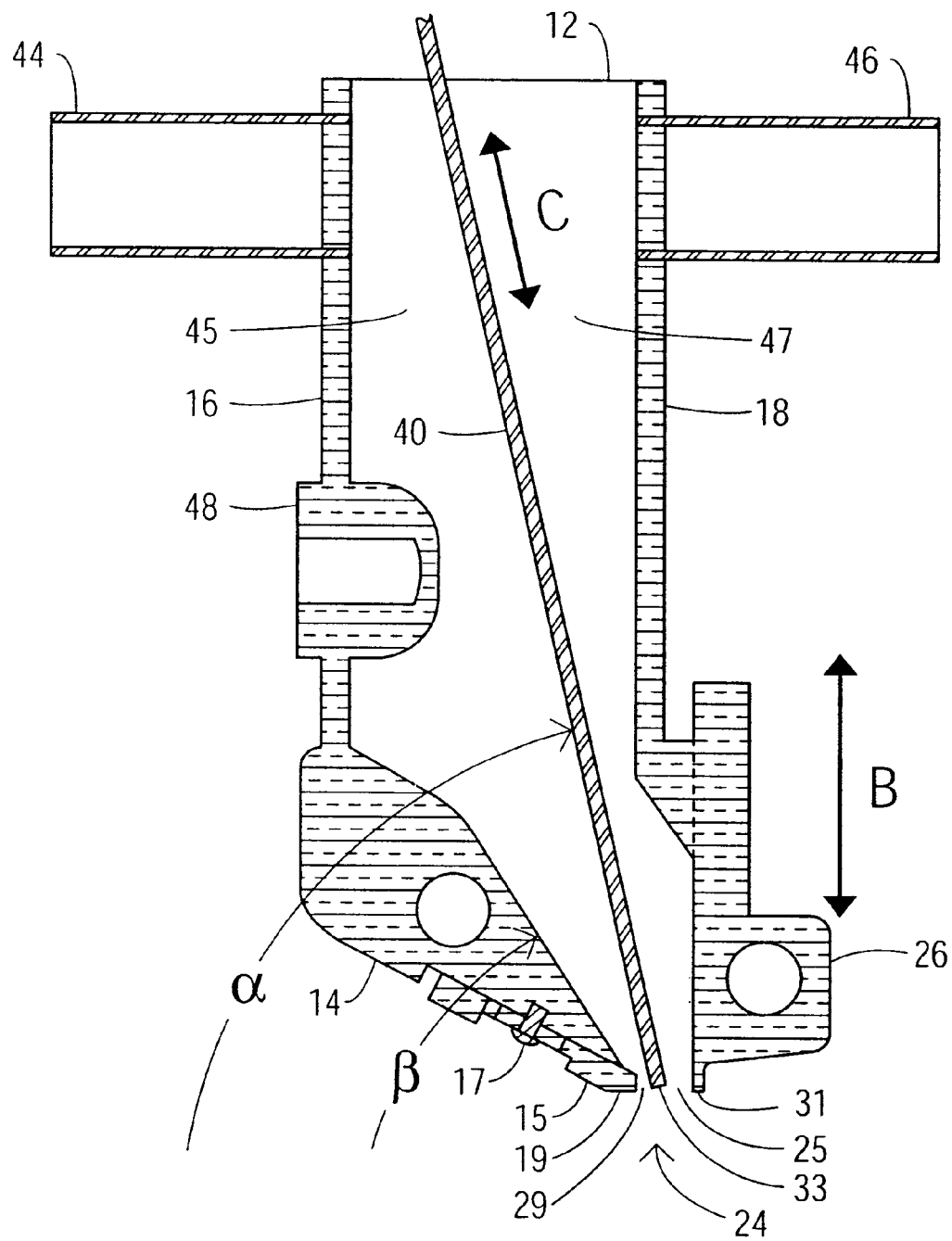
FIG. 2 is cross-sectional view through line 2—2 of FIG. 1.
Figure 3:
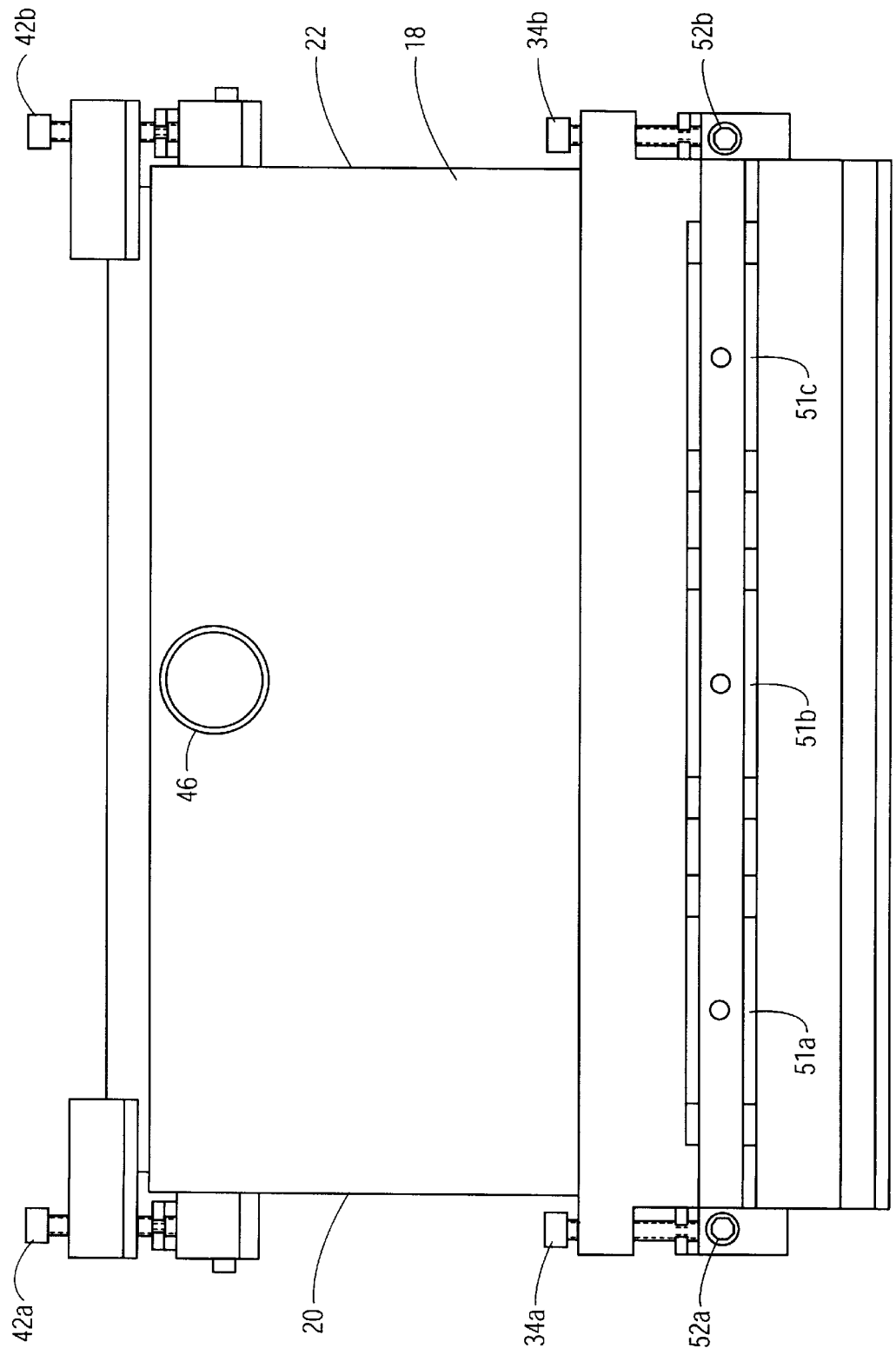
FIG. 3 is a front view of a gelatin spreader box of the present invention.
Figure 4:
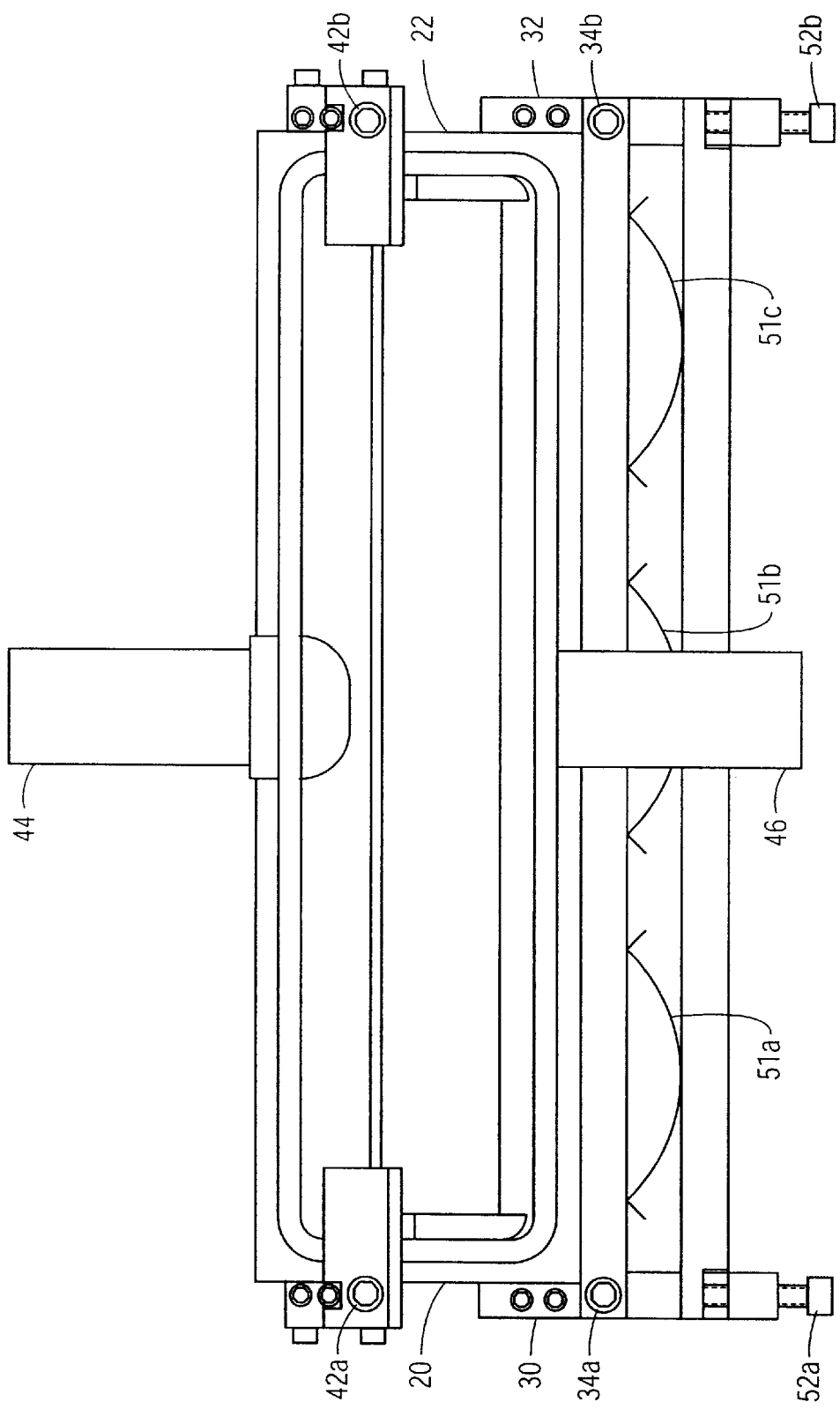
FIG. 4 is a top view of a gelatin spreader box of the present invention.
Figure 5:
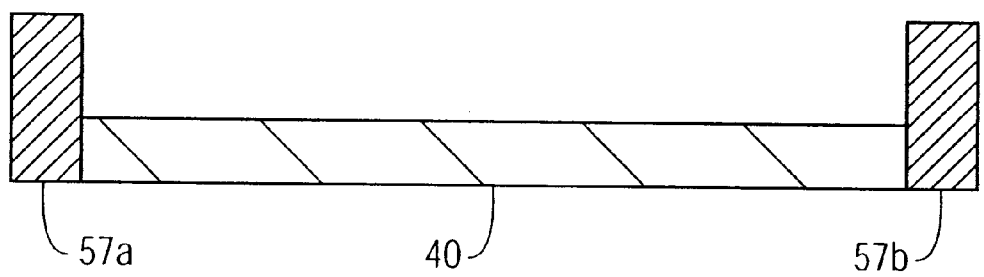
FIG. 5 is cross-sectional view of a plate of a height adjustable gate of the present invention.
Figure 6:
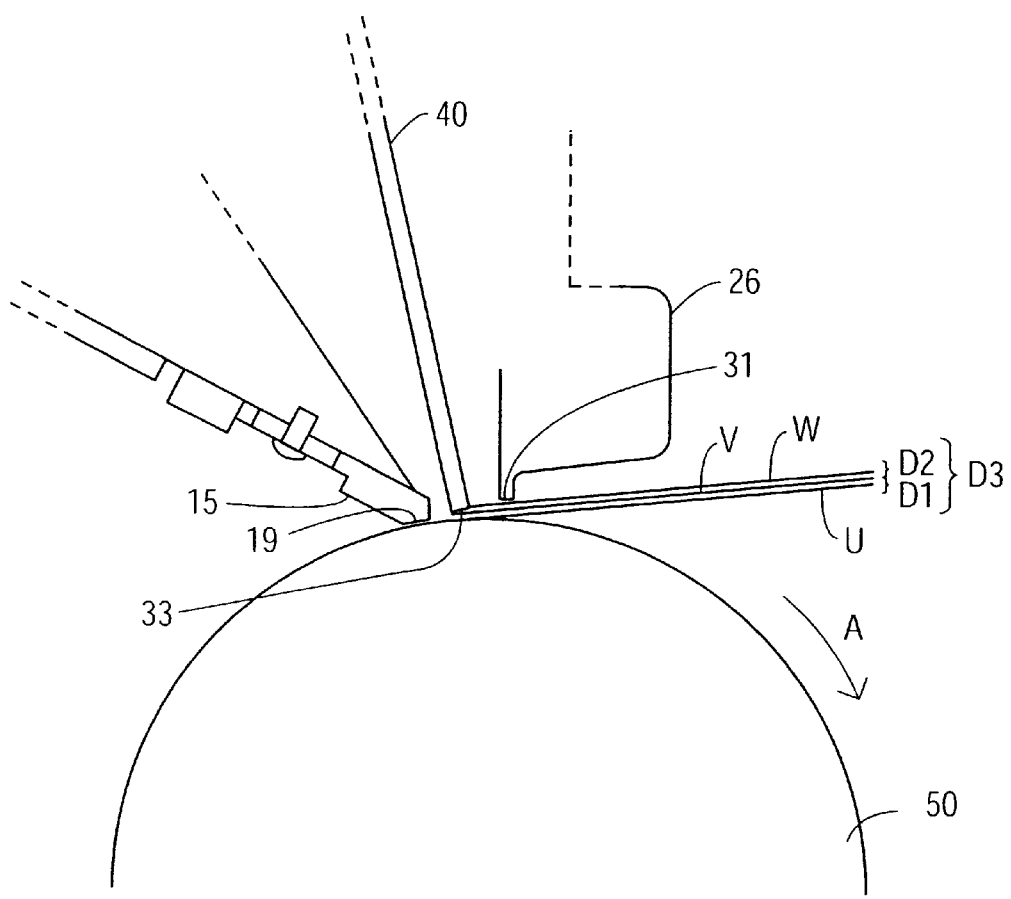
FIG. 6 is a cross-sectional schematic view of a portion of a gelatin spreader box of the present invention.

Plate 40 preferably slopes downwardly from top 12 to an opening 24 at an angle which facilitates the extrusion, from opening 24, of gelatin contained in chamber 47 of spreader box 10. In an alternative embodiment, plate 40 can extend from back side 16 to opening 24. The slope of plate 40 as an angle $\alpha$ relative to a horizontal line X parallel to the ground, as depicted in FIG. 2, can vary from about 1 degree to about 89 degrees. Preferably $\alpha$ is about 10 degrees to about 70 degrees and most preferably from about 45 degrees to about 60 degrees.

Similarly, bottom 14 is preferably downwardly sloped from back side 16 to front side 18 to facilitate the extrusion of gelatin contained in chamber 45 of spreader box 10. The slope of bottom 14 as an angle $\beta$ relative to a horizontal line X parallel to the ground, as depicted in FIG. 2, can vary from about 1 degree to about 89 degrees. Preferably $\beta$ is about 10 degrees to about 70 degrees and most preferably from about 30 degrees to about 45 degrees. Bottom 14 includes a gelatin backflow restricter 15 which can be integrally formed as part of bottom 14. Restricter 15 has a doctoring blade 19 which has a preferably flat surface for closely engaging the surface of rotary die drum 50 for preventing molten gelatin from flowing back against the motion of rotation of rotary die drum 50. In a preferred embodiment restricter 15 is removably affixed to bottom 14 by screw 17, providing for convenient replacement of restricter 15 after wear of doctor blade 19.

Bottom 14 of spreader box 10 includes opening 24. Opening 24 has a front portion 25 and a rear portion 29. Spreader box 10 contains gelatin, preferably molten, which can be extruded as a first layer from chamber 47 through opening 25 and extruded as a second layer from chamber 45 through opening 29. The first layer has a thickness controlled by first height adjustable gate 26 and the second layer has a thickness controlled by second height adjustable gate 28. The second height adjustable gate 28 is disposed at least partially across opening 24 and divides opening 24 into front portion 25 and a rear portion 29. The second height adjustable gate 28 preferably includes a plate 40 which is disposed within spreader box 10.

Plate 40 has a lower edge 33. Lower edge 33 is about $\frac{1}{32}$" to about $\frac{1}{4}$" in width and more preferably about $\frac{1}{16}$" to about $\frac{1}{8}$" in width. Lower edge 33 is preferably flat and preferably is tangent to the surface of rotary die 50. However, lower edge 33 can form an angle less than or greater than the angle formed by lower edge 33 when it is tangent to the surface of rotary drum 50.

The distance between lower edge 33 and the surface of rotary die drum 50 restricts the thickness of the molten gelatin between lower edge 33 and the surface of rotary die drum 50, thereby fixing the thickness of the second gelatin layer extruded through opening 29. This thickness is depicted as D1 in FIG. 6. D1 is defined as the distance between line U tangent to the surface of rotary drum 50 and line V which is parallel to lower edge 33. The viscosity of the molten gelatin combined with the centripetal force supplied by the rotary die drum pulls a continuous layer of molten gelatin between lower edge 33 and the surface of rotary die drum 50. Typically, the thickness of the gelatin layer is between about five thousandths of an inch ("mils") and about 50 mils. More preferably it is between about 10 mils and about 25 mils. In a most preferred embodiment the gelatin layer is about 15 mils. The height of plate 40 can be adjusted by height adjustment mechanism 42a and/or 42b which can control the height of plate 40 independently of first height adjustable gate 26. Height adjustment mechanisms 42a and/or 42b are preferably screws which engage plate 40 and move plate 40 up and down in the direction of arrow C as depicted in FIG. 2. Screws 42a and 42b engage threads disposed on the sides of plate 40. Preferably screws 42a and 42b remain stationary and the threads on plate 40 ride up and down the stationary threads. Alternatively, the screws may move up and down. Preferably the threads on plate 40 are disposed above top portion 12 to prevent fouling by molten gelatin. The thread pitch is selected to be fine enough to allow for mil increment adjustments of plate 40. The proper adjustment of the screws can be checked by measurement of the extruded layers with a ribbon gauge or observation of the layers under a comparator microscope as is known in the art.

In another embodiment, electronic height adjustment means, as would be known to those of ordinary skill in the art, can be used to vary the height of plate 40. The height adjustment of plate 40 thereby varies the distance between lower edge 33 and rotary die drum 50.

In an alternative embodiment the thickness of the gelatin layer extruded between lower edge 33 and the surface of rotary die drum 50 can be varied by lowering or raising the rotary die drum 50 relative to lower edge 33, while lower edge 33 remains stationary. In an alternative embodiment the thickness of the gelatin layer extruded between lower edge 33 and the surface of rotary die drum 50 can be varied by raising or lowering the entire spreader box 10 and not just plate 40. Combinations of the above can also be used.

A third or more height adjustable gate similar to plate 40 can be disposed within spreader box 10 to form a third or more compartments for containing gelatin and from which a third or more gelatin layer can be extruded similarly to the manner described for the second height adjustable gate 28. An additional gelatin supply line would also be used to supply molten gelatin to this third compartment.

First height adjustable gate 26 is preferably affixed at a first end 30 and at a second end 32 to opposed sides 20 and 22. However, gate 26 can be affixed intermediate of opposed sides 20 and 22. Gate 26 is preferably affixed to a height adjustment mechanism 34*a* and/or 34*b* which in one embodiment controls the space between a lower edge 31 of gate 26 and the surface of rotary die drum 50. Lower edge 31 is about 1/32" to about 1/4" in width and more preferably about 1/16" to about 1/8" in width. Lower edge 31 is preferably flat, but may be slightly rounded, and preferably is tangent to the surface of rotary die 50. However, lower edge 31 can form an angle less than or greater than the angle formed by lower edge 31 when it is tangent to the surface of rotary drum 50.

By adjusting the distance between lower edge 31 and the surface of rotary die drum 50 the thickness of the first gelatin layer can be varied. The thickness of the first gelatin layer is determined by both the height of the second height adjustable gate 28 and the height of the first height adjustable gate 26. This thickness is depicted as D2 in FIG. 6. D2 is defined as the distance between line V which is parallel to lower edge 33 and line W which is parallel to lower edge 31. D2 can also be determined as the difference between D3, the height from the surface of the rotary drum to lower edge 31 and D1 as defined above. For example, if lower edge 31 is thirty thousandths of an inch above rotary drum 50 and lower edge 33 is fifteen thousandths of an inch above rotary drum 50, the first gelatin layer will be fifteen thousandths of an inch thick as will the second gelatin layer. If lower edge 31 is thirty five thousandths of an inch above rotary drum 50 and lower edge 33 is fifteen thousandths of an inch above rotary drum 50, the first gelatin layer will be twenty thousandths of an inch thick and the second gelatin layer will be fifteen thousandths of an inch thick.

In a particular embodiment, the height adjustment mechanism 34*a* and/or 34*b* is at least one screw which engages gate 26 and which when turned raises or lowers gate 26 relative to rotary drum 50. Other mechanisms such as but not limited to a clamp which can be loosened to release and tightened to engage gate 26 which can be slid to different heights above rotary drum 50 can be used to adjust the height of opening 24. Less preferably, other fasteners such as Velcro® or adhesives can be used to set the height of first height adjustable gate 26. In another embodiment electronically controlled height adjustment means, as would be known to those of ordinary skill in the art, can be used to adjust the height of gate 26.

First gate 26 is preferably formed of a heat conducting and durable material preferably a metal. However, other materials such as but not limited to plastic, composites and combinations thereof can be used.

First gate 26 is preferably affixed by spring tension to spreader box 10 by elliptical leaf springs 51*a–c*. The spring tension prevents any side to side and back and forth movement of first gate 26. The tension of the leaf springs on first gate 26 can be controlled by adjustment screws 52*a* and 52*b*. This mechanism for affixing first gate 26 to spreader box 10 provides the ability to quickly and conveniently removing first gate 26 for routine maintenance.

Various gelatin shell masses can be prepared, depending on the fill properties, climatic conditions, and end use. Typically gelatin compositions include the same basic ingredients, namely, gelatin, a plasticizer such as glycerin, water, and optionally preservatives. The gelatin composition can also include sorbitol. Colorants as are known in the art can be included. The formulations of gelatins are well known to those of ordinary skill in the art. The same or different gelatin compositions can be used to form the different layers of the softgels of the present invention. Multiple layer softgels of the present invention can have layers which are the same thickness or a different thickness from each other or combinations thereof if three or more layers comprise the softgel.

Shell formulations are discussed in Van Hostetler and J. Q. Bellard noted below as well as in "Advances in Softgel Formulation Technology", M. S. Patel, F. S. S. Morton and H. Seager, *Manufacturing Chemists,* July 1989; "Soft Elastic Gelatin Capsules: A Unique Dosage Form", William R. Ebert, *Pharmaceutical Technology,* October 1977; "Soft gelatin capsules: a solution to many tableting problems", H. Seager, *Pharmaceutical Technology,* September 1985; U.S. Pat. No. 4,067,960 to Fadda; U.S. Pat. No. 4,198,391 to Grainger; U.S. Pat. No. 4,744,988 to Brox; and U.S. Pat. No. 4,780,316 to Brox. These references are incorporated herein in their entireties by reference.

The most common modern manufacturing process involved in the preparation of softgels is a continuous method whereby two gelatin ribbons pass between twin rotating dies. As the ribbons meet, the liquid to be encapsulated is precisely injected between them by injection means as known to those of ordinary skill in the art. The capsule halves are sealed and ejected by the continuous rotation of the dies. See P. Tyle, Specialized Drug Delivery Systems, Marcel Dekker, Inc. (1990) for a general discussion of softgel manufacturing and production technology, in particular, Chapter 10 by Paul K. Wilkinson and Foo Song Hom.

The present invention provides a system which modifies this standard technique by providing two gelatin sheets which each are composed of at least two layers of gelatin, one sheet being composed of a first and second layer and the other sheet being composed of a third and fourth layer. Such multiple layer softgels can also be referred to as having stacked layers. Each sheet is formed by a spreader box of the present invention. The two layers of gelatin extruded from the spreader box do not mix together due to both the viscosity of the gelatin in each layer and the rapid cooling of the lower layer which is in contact with rotary die drum 50 just prior to the point at which the second layer is deposited on the first lower layer. The second layer can either partially overly or completely overly the first layer of the softgel. If the second layer partially overlays the first layer it can partially overly the first layer at any region between the ends of the softgel. The second layer can also be deposited in more than one region on the first layer to form, for example, stripes on the first layer. Such partial coating of or striping of the softgels can be formed by providing for a slot or slots in the first height adjustable gate which restrict the flow of gelatin forming the second layer to some portions of the first layer and allows this flow at other portions. The addition of yet another or additional layers is accomplished similarly. The fusing together of two sheets of gelatin each composed of two layers results in formation of a softgel capsule having two continuous layers. An environmental seam 60 resulting from the above-described fusing is illustrated. in FIGS. 7*a* and 7*b*.

Typially, each sheet will be comprised of gelatin. However, in particular embodiments of the present invention, the layer of each sheet which forms the outer coating of the softgel capsule can comprise film coating materials other than gelatin which are compatible with gelatin. For example, a layer of cellulose acetate phthalate ("CAP") alone or CAP mixed in gelatin can be coated as the outer gelatin layer. Preferably, from about 1% to about 10% CAP can be used. More preferably, from about 3% to about 5% CAP can be used. Alternatively, for example, methyl cellulose, ethyl cellulose and hydroxypropylmethyl cellulose can be used.

The typical rotary die process, which requires a flowable liquid or fill, is readily adaptable to accommodate the multiple gelatin layer softgels of the instant invention. After the rotary die process is used to thereby produce gelatin shells having multiple layers, the resulting capsules are typically washed with an evaporatable solvent. Thereafter, the capsules are typically tumble dried in a series of hollow drums with perforated walls.

It is, for example, during this drying stage that multiple layer gelatin capsules which include a clear layer coating a layer including at least two colors can prevent the unwanted transfer of darker color to lighter color portions of the softgels. Room air (25° C.) is continuously pumped through the rotating drums. By the time the capsules exit this process, all of the solvent used in washing has typically been evaporated, and a large proportion (50–60%) of the water from the gelatin shell has been removed. Recent developments in drying include bypassing the drum drying stage and having the capsules dried in a drying tunnel or room as discussed below.

After the capsules exit the last drying drum, the capsules are typically spread on drying trays. The final drying phase for softgels is typically accomplished by passing the drying trays through drying tunnels or into drying rooms. Stacks of trays are inserted into drying tunnels or drying rooms, in which controlled temperature air (21°–24° C.) and low relative humidity (20–30%) is continuously circulated. Although additional water can be removed from dry capsules by further heating, for example at 40° C., such a procedure has not been found to be practical or necessary. See Van Hostetler and J. Q. Bellard in *The Theory and Practice of Industrial Pharmacy*, "Capsules", (1970), Chapter 13 at pages 346–383, and in particular at page 380.

The drying time, for most softgels, is 16–24 hours, but can be slightly longer if the softgels are over 20 minims in size or if the softgels contain a non-oily type liquid base. The Karl Fischer test is used for determining water content. The drying occurs typically at about 21° C. to about 24° C. and at a relative humidity of about 20% to about 40%.

Softgels permitted to come to water equilibrium in this controlled environment are considered "dry". After drying, the capsules are typically inspected and finished using varied known techniques.

A typical gelatin shell formulation includes 47 wt % gelatin, 15 wt % glycerin (USP), and 38 wt % water, optionally with additional colorant materials. Other shell formulations can readily be prepared by one of ordinary skill in the art.

The invention is further illustrated by reference to the following non-limiting examples. The following examples show compositions for each of two layers in a two layer softgel.

EXAMPLE 1
Color Rub Off Protection

| First Layer: | Gelatin | 30%–50% |
|---|---|---|
| | Plasticizer | 15%–35% |
| | Water | 15%–40% |
| Second Layer: | FD&C Red 40 | 0.01%–0.4% |
| | Gelatin | 30%–50% |
| | Plasticizer | 15%–35% |
| | Water | 15%–40% |
| Second Color: | Titanium Dioxide | 0.1%–1% |
| | Gelatin | 30%–50% |
| | Plasticizer | 15%–35% |
| | Water | 15%–40% |

EXAMPLE 2
Different Permeability

| First Layer: | Colorant(s) | 0.01%–0.4% |
|---|---|---|
| | Gelatin | 30%–45% |
| | Plasticizer | 20%–35% |
| | Water | 20%–40% |
| Second Layer: | Colorant | 0.01%–0.4% |
| | Gelatin | 40%–50% |
| | Plasticizer | 15%–35% |
| | Water | 15%–40% |

EXAMPLE 3
Different Taste

| First Layer: | Gelatin | 30%–45% |
|---|---|---|
| | Plasticizer | 20%–35% |
| | Water | 20%–40% |
| | Flavoring | 0.05%–2% |
| | Sweetener | 0.1%–5% |
| Second Layer: | Colorant(s) | 0.01%–0.4% |
| | Gelatin | 40%–50% |
| | Plasticizer | 15%–30% |
| | Water | 15%–40% |

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A softgel capsule with content, having opposing ends comprising a first sheet that covers a first end, the first sheet comprising at least a first gelatin layer and a second gelatin layer, each layer having a uniform thickness, and a second sheet that covers a second end, the second sheet comprising at least a third gelatin layer, the third layer having a uniform thickness wherein the first and second sheets meet at a seam.

2. The softgel capsule of claim 1 further comprising a fourth gelatin layer that surrounds the third layer.

3. The softgel capsule of claim 2 wherein the first layer is adjacent the second layer and the third layer is adjacent the fourth layer.

4. The softgel capsule of claim 2 wherein the first and third layers are a first color and the second and fourth layers are a second color.

5. The softgel capsule of claim 2 wherein the first and third layers are colored and the second and fourth layers are uncolored.

6. The softgel capsule of claim 1 wherein the thickness of the first and second gelatin layers are the same.

7. The softgel capsule of claim 1 wherein the thickness of the first and second gelatin layers are different.

8. The softgel capsule of claim 1 wherein the first and second layers differ with respect to at least one property selected from the group consisting of degree of permeability, rate of dissolution, mouth feel and taste.

9. The softgel capsule of claim 1 formed by an apparatus comprising a device for forming the first sheet having at least two gelatin layers.

10. A softgel having two opposing ends divided at a seam having at least one sheet covering each end, the at least one sheet comprising at least two stacked gelatin layers of uniform thickness.

11. The softgel of claim 1 wherein the combined thickness of the first and second layers is approximately equal to the thickness of the third layer.

12. The softgel capsule of claim 2 wherein the first and third layers are uncolored and the second and fourth layers are colored.

13. The softgel capsule of claim 2 wherein the first and third layers are a cellulose derivative and gelatin mixture and the second and fourth layers are gelatin.

14. The softgel capsule of claim 13 wherein the first and third layers are comprised of from about 1% to about 10% cellulose acetate phthalate.

15. The softgel capsule of claim 2 wherein the first and second sheets respectively further comprise a fifth layer surrounding the first layer and a sixth layer surrounding the third layer.

16. The softgel capsule of claim 15 wherein the second, fourth, fifth, and sixth layers are gelatin and the first and third layers are a cellulose derivative.

17. The softgel of claim 2 wherein the thickness of the third and fourth layers is the same.

18. The softgel of claim 2 wherein the thickness of the third and fourth layers is different.

19. The softgel of claim 1 wherein the first and third layers are colored and the second layer is uncolored.

20. A softgel capsule having opposing ends comprising:

a first sheet having at least a first gelatin layer that surrounds a second gelatin layer; and a second sheet having at least a third gelatin layer that surrounds a fourth gelatin layer, wherein the first and second sheets cover respective opposing ends of the softgel capsule and fuse together to form a seam.

21. The softgel capsule of claim 20 wherein the combined thickness of the first and second layers is about equal to combined thickness of the third and fourth layers.

22. The softgel capsule of claim 20 wherein the thickness of each layer is the same.

23. The softgel of claim 20 wherein the thickness of each layer is different.

24. The softgel of claim 20 wherein the first, third, and fourth layers are uncolored and the second layer is colored.

25. The softgel of claim 20 wherein the first and third layers are uncolored and the second and fourth layers are colored.

* * * * *